(12) United States Patent
Neto

(10) Patent No.: US 9,050,019 B2
(45) Date of Patent: Jun. 9, 2015

(54) PHARYNGEAL ULTRASOUND GUIDE

(76) Inventor: Luiz Ferreira Maracajá Neto, Brooklyn, NY (US)

( * ) Notice: Subject to any disclaimer, the term of this patent is extended or adjusted under 35 U.S.C. 154(b) by 392 days.

(21) Appl. No.: 12/777,158

(22) Filed: May 10, 2010

(65) Prior Publication Data

US 2011/0125026 A1     May 26, 2011

Related U.S. Application Data

(60) Provisional application No. 61/176,606, filed on May 8, 2009.

(51) Int. Cl.
| | | |
|---|---|---|
| A61B 8/14 | (2006.01) |
| A61B 8/06 | (2006.01) |
| A61B 8/08 | (2006.01) |
| A61B 8/12 | (2006.01) |
| A61B 8/00 | (2006.01) |
| A61B 17/24 | (2006.01) |
| A61B 17/34 | (2006.01) |
| A61B 19/00 | (2006.01) |

(52) U.S. Cl.
CPC ............... *A61B 8/06* (2013.01); *A61B 8/0833* (2013.01); *A61B 8/0841* (2013.01); *A61B 8/12* (2013.01); *A61B 8/42* (2013.01); *A61B 8/4281* (2013.01); *A61B 8/4422* (2013.01); *A61B 8/445* (2013.01); *A61B 8/488* (2013.01); *A61B 17/24* (2013.01); *A61B 17/3415* (2013.01); *A61B 2017/3486* (2013.01); *A61B 2019/5276* (2013.01)

(58) Field of Classification Search
USPC ......... 600/301, 325, 380, 393, 407, 423, 433, 600/434, 435, 437, 468, 470
See application file for complete search history.

(56) References Cited

U.S. PATENT DOCUMENTS

| | | | |
|---|---|---|---|
| 6,478,743 B1 * | 11/2002 | Jordfald et al. ............... | 600/462 |
| 2002/0066450 A1 * | 6/2002 | Bonutti .................... | 128/200.26 |
| 2004/0221853 A1 * | 11/2004 | Miller ...................... | 128/207.14 |
| 2007/0123824 A1 * | 5/2007 | Kaveckis ...................... | 604/118 |
| 2007/0135803 A1 * | 6/2007 | Belson ............................... | 606/1 |
| 2007/0198074 A1 * | 8/2007 | Dann et al. ................... | 623/1.11 |
| 2008/0234701 A1 * | 9/2008 | Morales et al. ............... | 606/139 |

* cited by examiner

*Primary Examiner* — Unsu Jung
*Assistant Examiner* — Michael N Fisher
(74) *Attorney, Agent, or Firm* — Lewis Rice LLC

(57) ABSTRACT

A pharyngeal ultrasound guide (PUG) to be placed inside the pharynx which allows the transmission of ultrasonic waves from a ultrasonic probe placed therein into the structures of the pharynx, throat, and major vessels; the technique of acquisition of the ultrasonic images and Doppler measurements using such a device; and the procedures which may be performed using the images.

3 Claims, 15 Drawing Sheets

PHARYNGEAL ULTRASOUND GUIDE

CROSS REFERENCE TO RELATED APPLICATION(S)

This Application claims the benefit of U.S. Provisional Patent Application Ser. No. 61/176,606, filed May 8, 2009, the entire disclosure of which is herein incorporated by reference.

BACKGROUND OF THE INVENTION

1. Field of the Invention

This disclosure is related with the field of diagnostic and interventional ultrasonography. Specifically to a pharyngeal ultrasound guide (PUG) to be placed inside the pharynx which allows the transmission of ultrasonic waves from a ultrasonic probe placed therein; the technique of acquisition of the ultrasonic images and Doppler measurements using such a device; and the procedures which may be performed using the images.

2. Description of Related Art

In physics, ultrasound refers to all acoustic energy with a frequency above the upper limit of human hearing; approximately 20,000 hertz. Typical diagnostic sonography scanners used for medical imaging operate in a frequency range of 2 to 18 megahertz, a hundred times or more greater than the limit of human hearing.

Ultrasonography (sonography) has become a widely used imaging technology in clinical medical science. While it initially was only used as a noninvasive diagnostic tool, ultrasound is now used in therapeutic procedures as well as being a visual guide in interventional procedures such as vascular access, nerve blockage, biopsies or fine needle aspirations. Ultrasound techniques have been used in different medical specialties. For example, diagnostic sonography is currently used in the fields of anesthesiology, cardiology, critical care, endocrinology, emergency medicine, gastroenterology, gynecology, obstetrics ophthalmology and urology, in addition to many other fields.

Despite its wide use across several medical disciplines, diagnostic sonography still remains an examiner-dependent procedure, requiring the knowledge of anatomy, physics of ultrasound and Doppler, functional ultrasound anatomy, and advanced invasive techniques.

In application, diagnostic sonography is based on the principle of piezoelectricity, a propriety of polarized molecules trapped within a crystal matrix. When stimulated by alternating electric current, molecules vibrate generating ultrasound. Conversely when an ultrasonic wave strikes the crystal, the resulting vibrations of polarized molecules generate alternating electric current.

Medical sonography, therefore, generally uses a probe containing one or more acoustic transducers to send strong, short pulses of ultrasound into a material, specifically different body tissues. The sound waves are partially reflected back to the transducer from the layer between body tissues with different acoustic densities, known as acoustic interface. The greater the difference between the acoustic impedances detected by the transducer, the larger the echo. However, if the pulse hits a gas-filled cavity (such as an airway or lung) or solids (such as bone), the density difference is so great that most of the acoustic energy is refracted or absorbed, distorting the image and inhibiting visualization of structures located deeper than the gas or solid impediment since the wave effectively cannot continue beyond the impediment.

Where the sound wave is reflected back, the probe detects the reflection as an echo. The echo waves vibrate the transducer and the transducer turns the vibration into electrical pulses that travel to a processor associated with the ultrasonic scanner where they are processed and transformed into an image. The time it takes to travel back to the probe is measured by the ultrasonic scanner and used to calculate the depth of tissue interface causing the echo. In addition to timing, the ultrasonic scanner also detects the strength of the echo and its focal length and uses these measurements to give the resultant image depth and clarity. Thus, structures of different density are shown as different colors, saturations, or tints. Once the scanner has determined these three things, it can create a digital image of the area being examined which can be read by one used to interpreting the different parts of the image as corresponding anatomical structures.

One of the advantages of diagnostic ultrasonography is its ability to image muscles, soft tissues, vessels, and organs very well and its particular ability for delineating the interfaces between solid and fluid-filled spaces in the body. Other advantages include that it is relatively non-invasive, renders images generally in real-time, is non-radiating, is inexpensive, is readily portable, and permits bedside evaluation.

The major disadvantages of ultrasonographic resonance technology relate to the poor image acquisition when bone or other solids, or gaseous space, exists between the transducer and the area of interest as due to the extreme differences in acoustic impedances between the gaseous and solid medium and the adjacent tissue, the area of interest is blocked from view. This often means that sonography is not useable for imaging certain structures of the body due to neighboring structures acting as blocks to the signals or that certain structures can only be imaged from certain directions.

In addition, ultrasonography is an operator-dependent technology and the images are often relatively difficult to acquire and interpret. Specifically the operator needs to understand how the densities and related images correspond to anatomical structures. As such, a high level of skill and experience is needed to acquire good quality images and make accurate diagnoses, sonography often requires additional specialized personnel to be used.

Due to its many advantages, ultrasonography is utilized in a number of different techniques the probes are often specifically designed for specific uses. Thus, there are provided, but not limited to, abdominal, pelvic, trans-vaginal, vascular, soft tissue, eye, trans-thoracic and trans-esophageal echocardiography (TEE), intra-operatory, echo-endoscopy, intravascular, and intracoronary probes. Some of these are designed for use external to the human body, while others are for internal use using natural or man made orifices to provide access.

Trans-esophageal Echocardiography (TEE) is currently used as a diagnostic and monitoring tool during the perioperative period of cardiac and several non-cardiac surgeries as well as for certain cardiac evaluations. TEE has generally become the standard of care for cardiovascular monitoring, diagnostic and guidance in cardiac and several non-cardiac surgical and interventional procedures.

In TEE, the transducer is placed in the esophagus. Since the esophagus runs behind the heart, the echo does not have to travel through the front of the chest, avoiding obstacles such as the ribs and lungs. Thus, it often offers a much clearer image of the heart, particularly, the back structures, than does a standard cardiac echocardiogram obtained by applying a transducer to the front of the chest.

TEE provides a more complete anatomic and functional evaluation of the heart and great vessels than external endocardigraphy. Owing to its advantages, such as being relatively non-invasive, real-time and bed-side, the usefulness of TEE as a monitoring tool has spread in cardiac and non-cardiac high risk procedures. Currently the multi-plane technology of 2D images and Doppler measurements which the TEE can provide are able to analyze: heart valves, aortic and pulmonary vessels, myocardial contractility, systolic and diastolic function, intra-cardiac shunts, air embolism, preload, volume responsiveness, after-load, cardiac output, renal artery blood flow, hepatic venous outflow, and functioning of ventricular assistance devices.

The pharynx is a fibromuscular tube which extends from the base of the skull to the lower border of the cricoid cartilage (at which point it becomes the esophagus). Portions of the pharynx lie posterior to the nasal cavity (nasal pharynx), oral cavity (oral pharynx) and larynx (laryngeal pharynx). The inner layer of the pharynx is comprised of mucosa. The outer layer of the pharynx is comprised by a group of constrictor muscles. The pharynx communicates with the air of the atmosphere through the oral cavity and nasal cavity and serves as the airway. The inner surface of the pharynx is generally irregular due to the cavities and anatomic structures present such as: nasal cavity, palate, oral cavity, base of the tongue, tonsils, epiglottis, valecula, cartilages and the opening of the glottis. The anatomic irregularities generally prevent adequate contact and stabilization of an ultrasonic probe within the region as it is very difficult, if not impossible, to avoid a probe in the area having significant air interference from air both within, and flowing through, the pharynx. For this reason, TEE probes, while common for imaging the heart from the esophagus, have not been used in imaging structures in the pharyngeal region of the neck or throat.

A central venous catheter is a catheter placed into large vein in the neck (the internal jugular vein), chest (the subclavian vein) or the groin (the femoral vein). Central venous access is required for central venous and pulmonary artery wedge pressure monitoring and for the placement of a transvenous cardiac pacing device. It might also be necessary for fluid infusion, blood transfusion and drug administration if a peripheral IV cannot be established. The central venous catheter insertion has associated complications such as, pneumothorax (air in the pleural space which may compress the lungs), hemothorax (blood accumulation in the pleural cavity, the body cavity that surrounds the lungs), air embolism, catheter embolization, infection, cardiac arrhythmias, cardiac tamponade and placement of the catheter in the wrong direction inside the vein. Some of these complications are severe enough to cause death.

One area in which diagnostic ultrasonography is developing is as a visual guide for central venous catheter placement to help reduce the incidence of complications such as those listed above. The ultrasound provides real-time images that are useful in the central venous catheter placement process. The incidence of complications is higher when using the blind technique compared to ultrasound guide techniques and therefore such imaging is generally a preferred process in the placement. The most common vein used to insert a catheter during cardiac surgery is the internal jugular vein, located in the neck.

As many major surgical procedures require central venous access, improved safety in the process is highly desirable. External ultrasound-guided puncture is considered state-of-the-art and standard of care for central line placement. The ultrasound surface probe that is currently employed in such guided techniques requires the use of gel on the surface of the skin to provide for clear image quality and a sterile cover sheath around the probe and its cable. In order to visualize the whole procedure including the insertion of needle, guide wire and catheter, it is necessary to use in-line technique, which means the ultrasound beam is aligned with the longitudinal axis of the vessel being imaged.

Using a surface probe in such a fashion it is necessary an additional professional to hold the probe still in the longitudinal view of the jugular vein while a wire guide is inserted through a needle as the probe must remain in the puncture area to provide real time imaging. The preparation process prior to the puncture therefore may be time-consuming and may increase the risk of bacterial contamination as the skin break, which is necessarily present in the insertion of the needle, is necessarily close to the external ultrasound device and may be in contact with the ultrasound gel used to capture the image.

Many of the problems of external ultrasound can be avoided by use of an internal ultrasound probe which can be placed within the neck prior to the procedure being performed. However, while a TEE probe is capable of being placed in the neck and passes through the neck on its way to the esophagus, a TEE probe has been generally unable to image the structures of the neck with any precision.

SUMMARY OF THE INVENTION

Due to these and other problems in the art, disclosed herein, among other things, is an embodiment of a Pharyngeal Ultrasound Guide (PUG) device comprising: a hollow flexible shaft comprising two ends and an elongated body therebetween; a balloon arranged at a first of the two ends, the balloon being sized and shaped for placement in a pharyngeal region of a human and having an internal volume, the hollow shaft extending through the balloon; an external compartment including an ultrasound transmission medium; and a connecting tube interconnecting the external compartment and the balloon; wherein, the ultrasound transmission medium is transferred from the external compartment into the internal volume of the balloon after the balloon is placed in the pharyngeal region of the human so as to allow an ultrasound probe placed within the hollow shaft to image an adjacent region of the human.

In an embodiment of the device, the ultrasound probe comprises a Trans-Esophageal Echocardiography (TEE) probe.

In an embodiment of the device the balloon is generally pear shaped with the narrower portion arranged closer to the first end of the two ends.

In an embodiment of the device the ultrasound transmission medium is a liquid or gel.

In an embodiment, the device further comprises a casing attached to a second of the two ends, the casing having a greater rigidity than the hollow shaft.

In an embodiment of the device, an exterior surface of the casing is textured.

In an embodiment of the device, the hollow shaft includes an interior layer and an exterior layer with a volume therebetween, the volume surrounding the hollow interior of the hollow shaft.

In an embodiment of the device, the interior layer of the shaft corresponds to an interior layer of the balloon and the exterior layer of the shaft corresponds to an exterior layer of the balloon so that the shaft and the balloon are co-formed.

In an embodiment of the device the volume between the interior layer and the exterior layer of the hollow shaft is in fluid communication with the internal volume of the balloon.

There is also described herein, in an embodiment, a device for imaging the structure of the throat comprising: a pharyngeal ultrasound guide (PUG) device including: a hollow shaft comprising two ends and an elongated body therebetweeen;

and a balloon arranged at a first of the two ends, the balloon being sized and shaped for placement in a pharyngeal region of a human and having an internal volume including an ultrasound transmission medium; an ultrasound probe, the probe being placed within the hollow shaft so as to be in contact with the balloon such that ultrasound waves generated by the ultrasound probe are directed into the ultrasound transmission medium.

There is also described herein, in an embodiment, a method for imaging the structure of the throat comprising: providing a pharyngeal ultrasound guide (PUG) device, the device including: a hollow shaft comprising two ends and an elongated body therebetweeen; and a balloon arranged at a first of the two ends, the balloon being sized and shaped for placement in a pharyngeal region of a human and having an internal volume for enclosing an ultrasound transmission medium; providing an ultrasound probe; placing the probe within the hollow shaft and the balloon; positioning the probe and PUG assembly within the pharyngeal region of a human; transferring an ultrasound transmission medium into the internal volume after the positioning is complete so that the balloon fills the pharynx of the human; activating the probe so that an ultrasound wave can pass from the probe, into the balloon, through the medium, and into the pharynx without passing through air; and interpreting the ultrasound wave so as to provide an image of a portion of a throat of the human.

In an embodiment the method further comprises: placing a metallic object on a skin surface of the human adjacent the throat, the metallic object being contacted by the ultrasound wave and provided on the image.

In an embodiment of the method, the metallic object is visualized at a plurality of locations and the locations are connected by a marking placed on the skin.

In an embodiment of the method, the marking provides a guide for a needle puncture and placement.

In an embodiment of the method, the ultrasound wave is used to calculate a blood flow rate.

In an embodiment of the method, the ultrasound probe comprises a Trans-Esophageal Echocardiography (TEE) probe.

In an embodiment of the method, the TEE probe is advanced beyond the balloon and into the esophagus after the image is created.

In an embodiment of the method, the image is used for a needle puncture and catheter placement.

BRIEF DESCRIPTION OF THE DRAWINGS

FIG. 12A provides a picture of metallic object on the skin surface and a dermagraphic pen marking the inferior dot at the exact point in which the ultrasound beam is located. Below follows the respective ultrasonic image of acoustic shadow on the right side of the screen, corresponding to the lower third of the ultrasonic field.

FIG. 12B provides a picture of a metallic object on the surface and a dermagraphic pen marking the superior dot at the exact point in which the ultrasound beam is located. Below follows the ultrasonic image of the acoustic shadow on the left side of the screen, corresponding to the upper third of the ultrasonic field.

FIG. 12C provides a picture of the needle being introduced into the skin aligned with a straight line which connects the superior and inferior dots.

FIG. 12D provides the ultrasonic image of the needle being introduced into the jugular vein.

DESCRIPTION OF THE PREFERRED EMBODIMENT(S)

Figure 1:
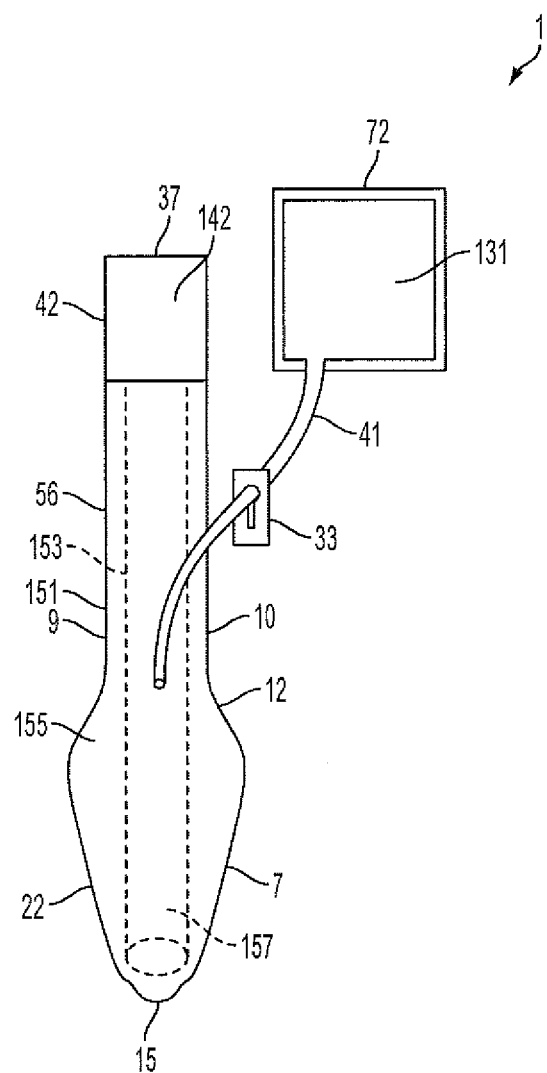
FIG. 1 provides a drawing of the orthogonal front side view of an embodiment of a Pharyngeal Ultrasound Guide (PUG) device.

The close anatomical relationship between the walls of the pharynx and vessels of the neck should allow an ultrasound probe to obtain the ultrasonic images of structures in the throat and neck as ultrasound waves which enter the pharynx are not blocked by solid or gas structures prior to the relevant vessels. Specifically, images of the carotid artery and jugular vein should be relatively clear. However, the air present in the pharynx's lumen has so far prevented the proper ultrasound transmission from the probe into these structures and thus has not allowed a probe to be used in imaging structures of the neck. Thus, such imaging has traditionally only been performed by external probes. Further, anatomical differences between individual users means that image artifacts and edge effect due to air are not consistent and therefore can render the images near impossible to interpret.

Trans-Esophageal Echocardiography (TEE) examination of the heart and chest is feasible due to the collapsed walls of the esophagus (absence of air as the esophagus is below the trachea) and the close anatomical relationship of the esophagus and the heart. However, the walls of the pharynx (which is above the trachea) are not naturally collapsed and the air present prevents transduction of ultrasound waves outside of the pharynx.

As described in further detail in conjunction with the FIGS., There is provided herein a pharyngeal ultrasound guide (PUG) (1) which is designed to act as a bridge between an ultrasound probe (803), specifically a TEE probe (803), and the walls of the pharynx. Specifically, the PUG (1) provides a hollow sheath (56) within which the TEE probe (803) is placed. The sheath (56) is then encased in or is formed from an inflatable structure or balloon (22) which can include an adjustable amount of an ultrasound compatible medium (131). The assembly (850) is generally placed within the pharyngeal region, the balloon (22) is filled with medium (131) which displaces air between both the balloon (22) and the pharynx and the balloon (22) and the probe (803), and allows image acquisition of the neck structures. In the process, other benefits such as reducing the trauma caused by the TEE probe (803) insertion can also be realized.

Methods of use of the probe (803) and PUG (1) discussed herein are generally referred to as trans-pharyngeal ultrasound and may have applications such as, but not limited to, to guide central venous line placement, for per operative measurement of carotid blood flow, for guide clamp placement during carotid endarterectomy (CEA), for jugular bulb catheter insertion, for real time monitoring of carotid angioplasties, for cervical region biopsies, and for imaging of intervertebral discs and vertebral arteries. This disclosure will explain both various embodiments of the PUG (1) as well as exemplary methodologies for using the PUG (1) in ultrasound guided central line access and carotid blood flow measurements.

Transpharyngeal ultrasound using the TEE probe (803) associated with a PUG device (1) are believed to be generally preferred to the surface probe currently in use. This is particularly true in situations when the use of the central line and use of the TEE probe (803) is already necessary, such as cardiac and major non-cardiac surgeries as the transphryngeal ultrasound-guided access uses the same probe that is already used and present for TEE ultrasonography. By turning the multiplane angle of TEE probe (803) 90 degrees, it is possible to obtain longitudinal views of the jugular vein during needle, wire guide and catheter insertion with continuous, real-time imaging.

In addition, the TEE probe (803) may confirm the correct position of the tip of the catheter through the bicaval view during TEE examination. This type of procedure prevents patients from being exposed to radiation during chest X-rays for the simple purpose of checking the catheter position, as frequently occurs in intensive care units. With the 3D technology embodied in the newer TEE probes (803), the technology can be used to evaluate the neck structures using the PUG device (1).

With reference to FIGS. 1 through 10, embodiments of a PUG (1) will be described. Generally, in its most basic form, the PUG (1) comprises a flexible plastic polymer tube or sheath (56), a gel balloon (22) generally is formed therewith, and a tube connection (41) between the balloon (22) and a compartment (72) containing an ultrasound medium (131). It is contemplated that the PUG (1) will be used in conjunction with a TEE probe (803), or other endoscope/transducer probe known to those of skilled in the art which is designed to be inserted into the esophagus.

A TEE probe (803), or other known endoscope/transducer probe known to those of skilled in the art, will be used in conjunction with the PUG device (1) described herein to allow for the anatomic fitting of the TEE probe (803) into the pharynx and a resultant ultrasonic view of neck structures. It should be noted that the PUG (1) described herein may serve to provide for improved resolution in various other types of human anatomical structures as well, however, use for imaging the throat is seen as being particularly beneficial.

It is important to recognize that the PUG device (1) is different from a covering sheath for the TEE probe (803) and/or traditional endocavitiy covers or balloons used in echoendoscopy or endoscopic biopsies. The covering sheaths for the TEE probe (803) are used to avoid cross contamination and to protect the transducer and are not intended to improve image resolution. Further, the endocavity covering or balloons are not shape corrected to fit nor designed to facilitate the insertion into the pharynx and doesn't have an adjustable hollow to fit the TEE probe (803).

FIGS. 1-4 provide various views of an embodiment of a PUG (1). FIGS. 5-8 provide for similar views of an alternative embodiment. In FIGS. 5-8 the sheath (56) is depicted as translucent so the hollow interior (157) is visible when the TEE probe (803) is placed therein. As the embodiments generally share the same broad components, the two embodiments are discussed simultaneously. The PUG device (1) in these embodiments comprises a tube or sheath (56) having two layers or membranes (151) and (153). The inner layer (153) generally forms a generally cylindrical hollow opening through which the TEE probe (803) can pass and thus forms a hollow shaft for the TEE probe (803). The outer layer (151) may be arranged generally concentrically therewith and thus there is a internal space (155) between the two layers (151) and (153). The outer layer (151) has a shape generally similar to that of a human pharynx. A liquid compartment or balloon (22) with variable volume and rigidity exits between the two layers, at least at the fore end (15) of the device (1) and connects with an external compartment (72) via a connecting tube (41). The balloon (22) will generally be positioned so as to be toward a fore end (15) of the sheath (56).

It should be recognized that while the present disclosure contemplates that the sheath (56) and balloon (22) are relatively separate structures, they do not need to be and often will be formed together. Specifically, in an embodiment, such as those shown in FIGS. 1-8, the sheath (56) and balloon (22) are actually co-formed with each other with the sheath (56) having the internal layer (153) sized and shaped to enclose the TEE probe (803) and the outer layer comprising a narrower aft end (37) forming the sheath (56) which then forms the outer layer of the balloon (22) at the fore end (15). In the front view of FIG. 1, there is depicted the shaft (56) and the balloon (22), the external gel compartment (72), the thin connecting tube (41), and the releasing flow control (33). In this type of embodiment, the internal volume of the balloon (22) is also connected with the volume of the shaft (56) and thus the entire structure of the pug (1) may be inflated above the TEE probe which is placed in the hollow interior of the shaft (56).

In this embodiment, the shaft (56) and the balloon (22) of the PUG are made of double layer plastic polymer generally with a liquid medium (122) between the two layers (151) and (153). The flexible plastic polymer shaft (56) is generally constructed from polystyrene, polyvinyl chloride (PVC), polyethylene, polypropylene, polyetheretherketone (PEEK), or other plastic polymer known or discovered and utilized in the medical device sector. It is contemplated that these plastic may be used alone or together in a blend. Generally, the shaft (56) and balloon (22) will be of thinner construction and will lack internal rigidity. The inner layer (151) of the aft end (37), shaft (56), and balloon (22) is generally a hollow which surrounds the TEE probe (803). While depicted in the figures as circular in form, it is contemplated that the aft end (37) of the shaft (56), and the external shape of the shaft (56) itself, may be any shape that allows for insertion of the TEE probe into the tube and insertion of the tube into the human pharynx. Further, the shaft (56) will often lack rigidity to have a particular form and will collapse under its own weight.

In the embodiment of the PUG (1) illustrated FIGS. 1-4, the aft (37) end of the flexible polymer shaft (56) is surrounded by a firmer and stronger plastic casing (42). Generally, the casing (42) will only cover a small portion of the aft (37) end of the flexible polymer shaft (56). The casing (42) will generally provide sturdiness to the aft (37) end to facilitate the TEE probe insertion. It is also contemplated that in some embodiments the exterior surface (142) of the casing (42) will be ribbed or textured, to provide a surface that is easier for an individual to grasp and manipulate when the TEE probe (803) is being inserted into the flexible plastic polymer shaft (56). The casing (42) might also work as a bite blocker, avoiding hazards in the TEE probe (803) caused by a patient inadvertently biting down on the TEE probe (803). This can be particularly desirable where the shaft (56) lacks rigidity and could be cut if the patient bit into it.

Figure 2:
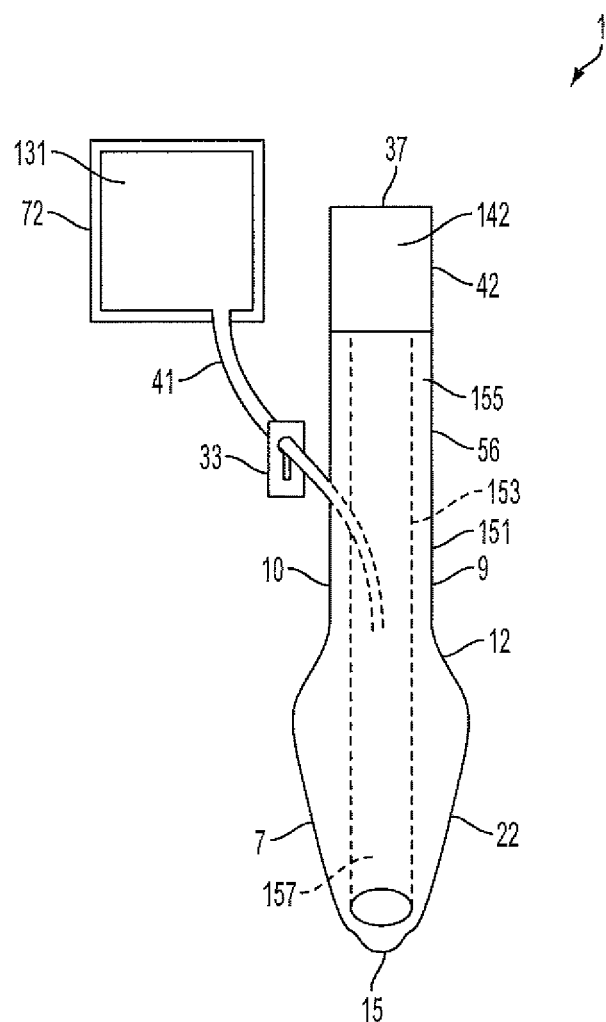
FIG. 2 provides a drawing of the orthogonal rear side view of the PUG device of FIG. 1.
Figure 3:
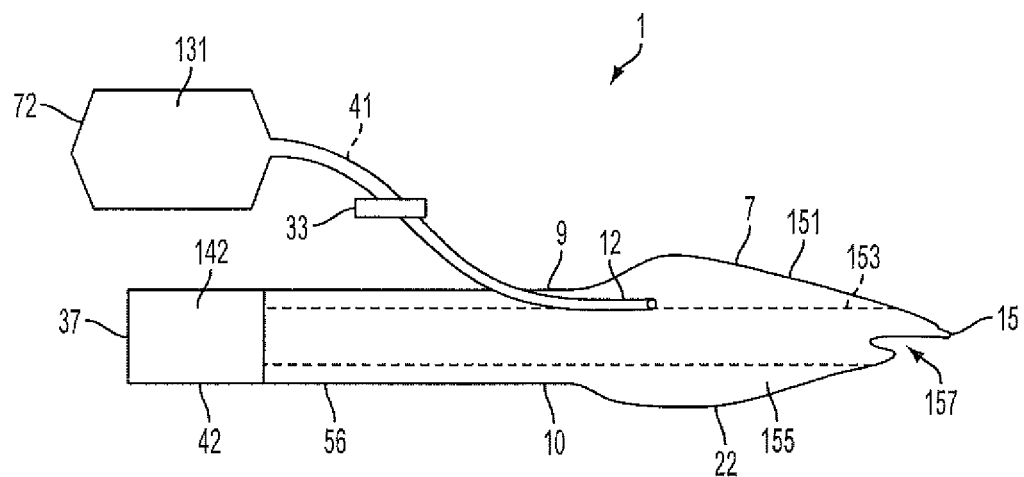
FIG. 3 provides a drawing of the orthogonal side view of the PUG device of FIG. 1.
Figure 4:
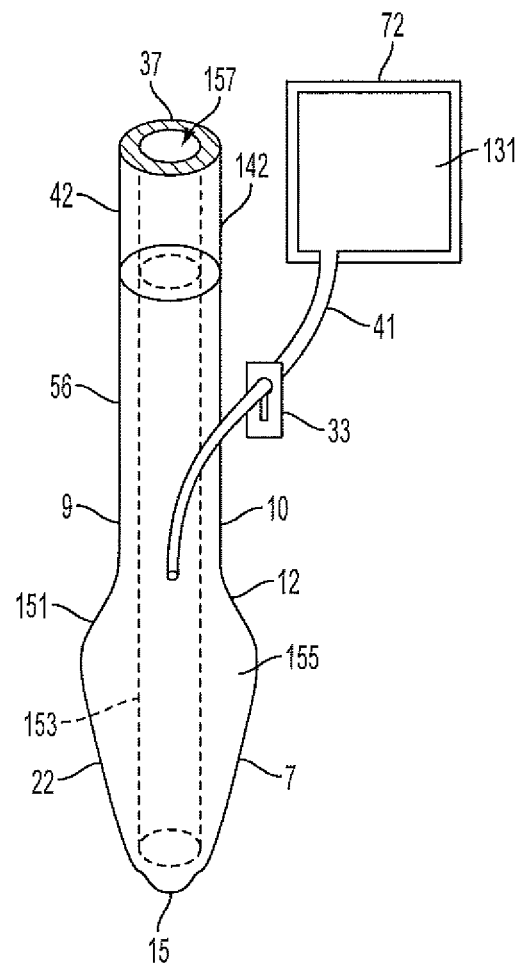
FIG. 4 provides a drawing of the perspective view of the PUG device of FIG. 1.
Figure 5:
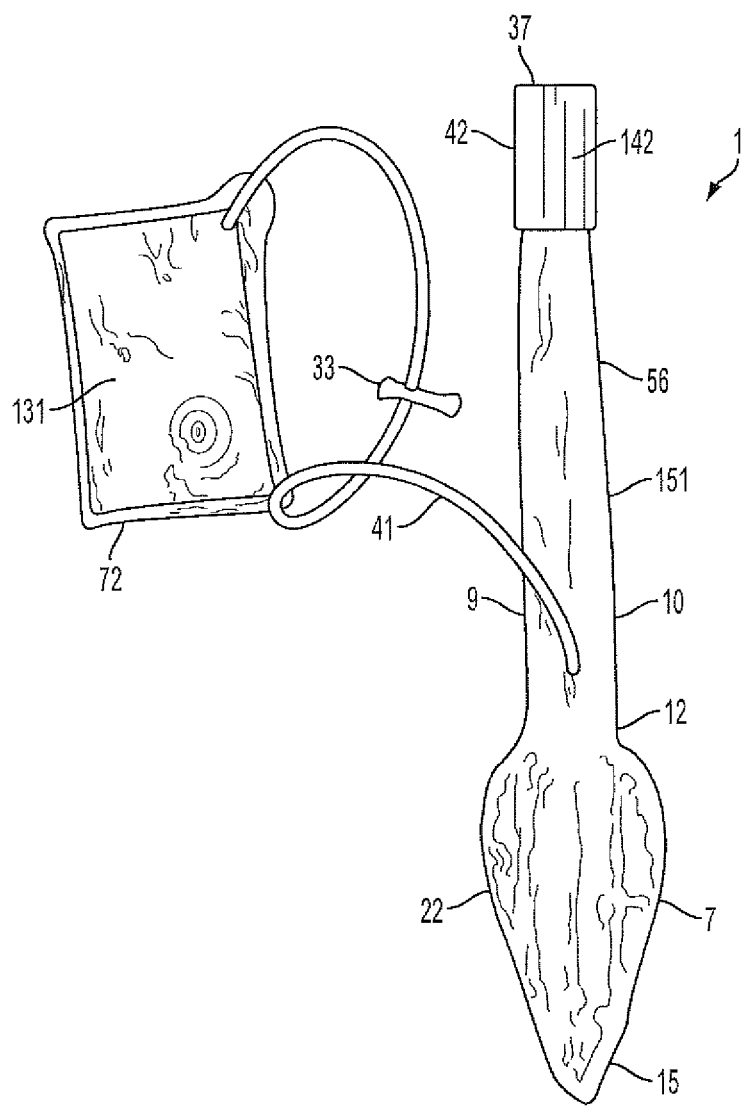
FIG. 5 provides a drawing of the frontal side view of another embodiment of a PUG device.
Figure 6:
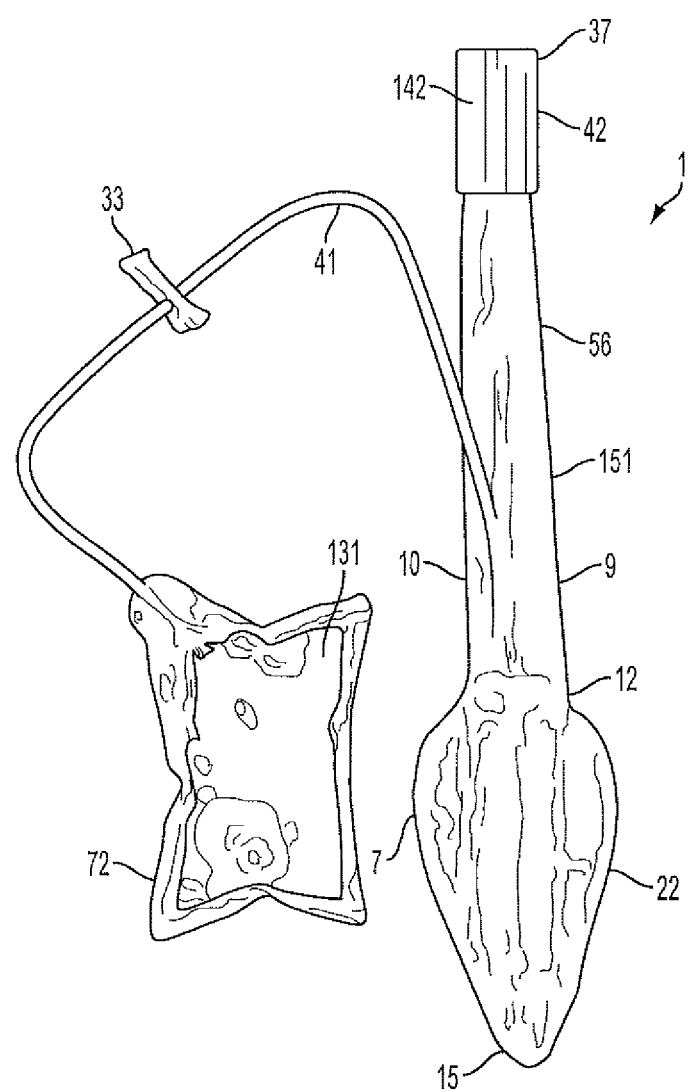
FIG. 6 provides a drawing of the rear side of the PUG device of FIG. 5.
Figure 7:
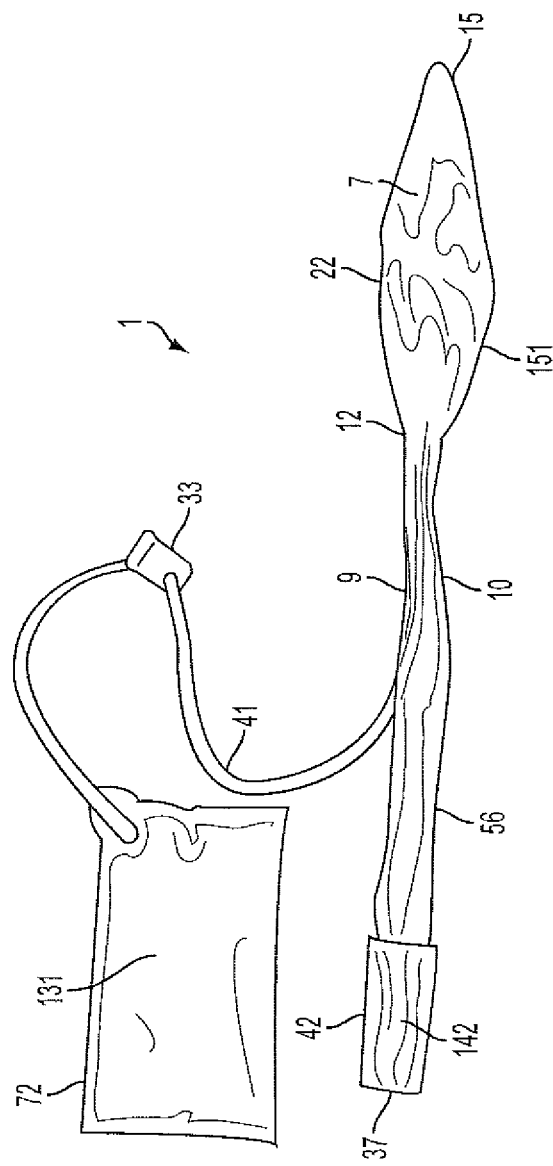
FIG. 7 provides a drawing of the lateral view of the PUG device of FIG. 5.

The fore (15) end of the flexible plastic polymer shaft (56) generally has a diagonally cut cross-section. Viewed from the lateral face of the PUG (1), as illustrated in FIG. 3, an opening of the cross-sectional cut at the fore (15) end is visible. From the posterior view, the posterior face of the fore (15) end is visible. The fore (15) end is generally triangular or loosely pear shaped in shape. In other words, the lateral edges (9) and (10) of the flexible plastic polymer shaft (56) form a triangular-like shape when viewed from the posterior face. When viewed from the anterior face, as illustrated in FIG. 1, the fore (15) end of the flexible polymer shaft (56) is an elongated opening, which resembles a circle positioned on a longitudinal axis of the flexible plastic polymer shaft (56), that has been elongated at its fore (15) end. In other words the balloon (22) resembles a pear shape having its broader end positioned towards the aft (37) end of shaft (56). The fore (15) end of the flexible polymer shaft (56) is located internally within the body of the gel balloon (22), as can be clearly seen from FIG. 1 illustrating the front view and FIG. 2 illustrating the posterior face The gel balloon (22) of the PUG (1) is generally ergonomically and anatomically correctly shaped and is designed to be filled with a ultrasound medium (131) which is a gel or liquid. The balloon (22) is generally located at the fore (15) end and includes an internal volume which freely communicates with the volume (155) between the inner (153) and outer (151) layers of the flexible plastic polymer shaft (56). As indicated, the shape of the gel balloon (22) is generally similar to a pear shape, having its broader end positioned towards the aft (37) end of the shaft (56). However, any anatomically correct shape balloon (22) that allows the insertion into the pharynx with the intention to adapt an ultrasonic probe and acquire ultrasonic images of the anatomic structures of the neck is contemplated.

The external layer of the gel balloon (22) in the present embodiment comprises a thin and flexible polyvinylchloride, or other applicable plastic polymer. The balloon (22) is then filed with an ultrasound transmitting medium which is generally a gel or liquid, such as, but not limited to, glycerin, water, commercial ultrasound gels, or similar products. Any substance known to those skilled in the art as an adequate media for ultrasonic wave transmission is contemplated between the two layers of the flexible polymer of the shaft (56), the balloon (22) and external compartment (72).

In one embodiment of the balloon (22) and shaft (56) will be inflatable through a thin connecting tube (41) linked to a external compartment (72) which contains a volume of material to be pushed into the gel balloon (22). In an embodiment, the external compartment (72) has generally the same volume as the gel balloon (22) and the balloon (22), tube (41) compartment (72) structure is sealed and thus the material can be moved between the balloon and tube, but is not intended to be removed from the system. In this embodiment the connecting tube (41) allows the passage of the medium (131) between the external compartment (72) and gel balloon (22) freely in accordance with the pressure gradients. Specifically, the external compartment may be positioned to allow the medium to flow under gravity, or may be squeezed (by hand or by a machine) to direct the medium (131) into the balloon (22). The embodiments of the FIGS. also include a flow control (33) attached to the connecting tube (41), which provides the maintenance of the desired volume inside the balloon (22). Specifically, once the balloon (22) is at the desired volume, the flow control (33) may be closed or locked to prevent the medium (131) from flowing between the balloon (22) and external compartment (72).

In application, the balloon (22) allows liquid or gel to be added to adapt the same device for use with different size pharynx and to each individual person upon which the device is used. The diameter of the hollow inside the shaft (56) and balloon (22) may also vary according the amount of liquid or gel which further adapts the PUG (1) to have the inner diameter (shape of inner membrane (153)) be alterable to handle TEE probes (803) of different sizes and brands. This disclosure also contemplates that a variety of differently sized PUG devices (1) may be provided which can be used with patients of widely different size such as may be the case between pediatric and adult patients.

As explained previously, one of the basic principles of ultrasound is that the sound wave requires generally liquid (as opposed to gas or solid) media for adequate wave transmittal and acquisition of images. As the pharynx is part of the respiratory system, a gas filled cavity in the human body, generally ultrasound diagnostic techniques are not available for viewing in this area of human anatomy because of the problems associated with ultrasound interfaces with gaseous media. However, the PUG (1) is designed to allow for the TEE to be placed in the shaft (56) which is then inside the material encased by the gel balloon (22) and/or shaft (56). By altering the volume of material in the balloon (22) once the PUG and TEE are in place in a patient, the balloon (22) can be made to fit relatively tightly within the pharynx and conform to the shape of the TEE (803) and the individual patient. In this way, the air space around the TEE (803), and the air space outside the PUG (1) (and thus the air interference from those spaces) is reduced or eliminated.

Now that the basic component parts of the PUG (1) have been disclosed and described, the methods of using the PUG (1) in ultrasound techniques will be discussed.

Figure 8:
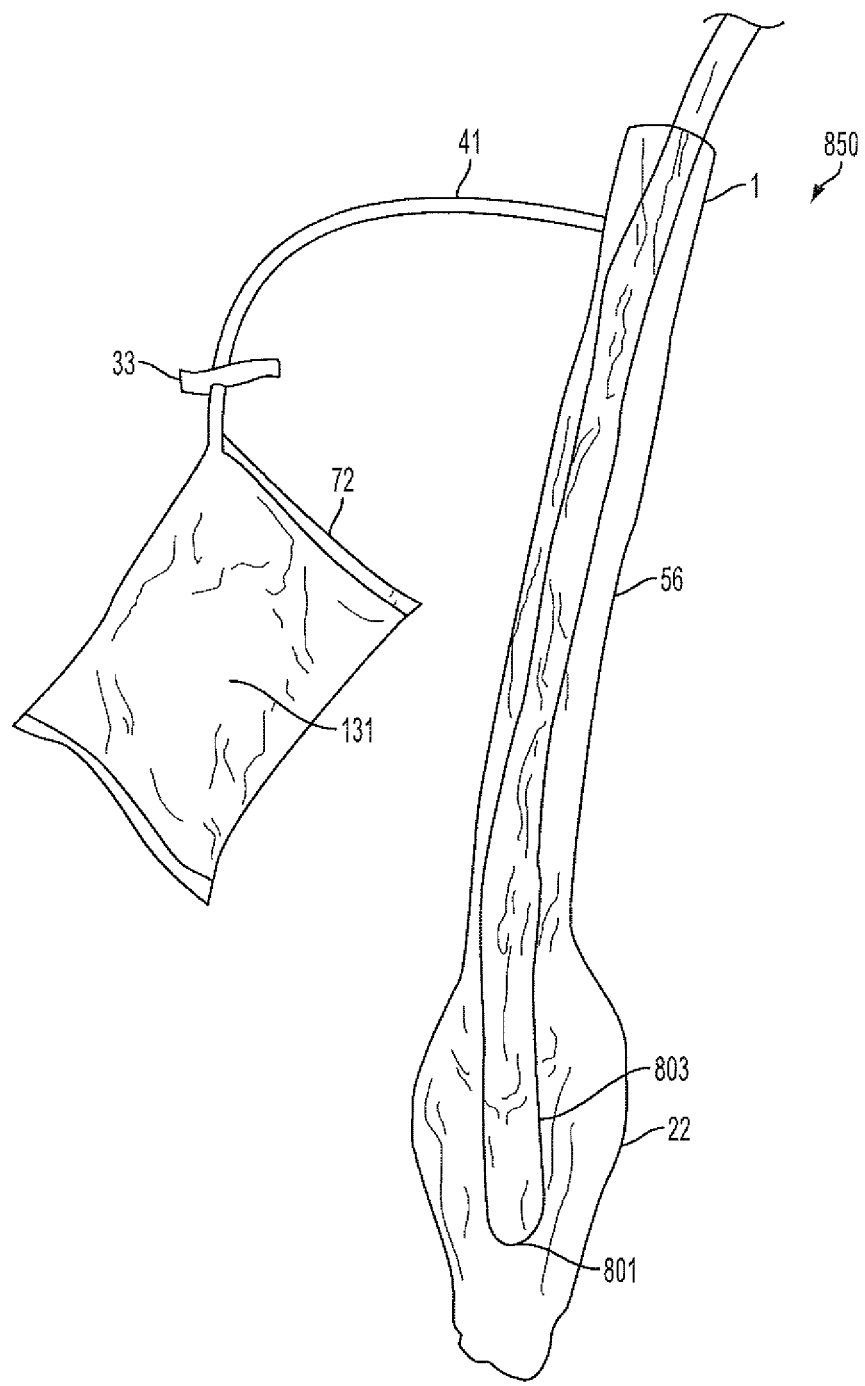
FIG. 8 provides a drawing of TTE probe insertion into an embodiment of a PUG device.
Figure 9:
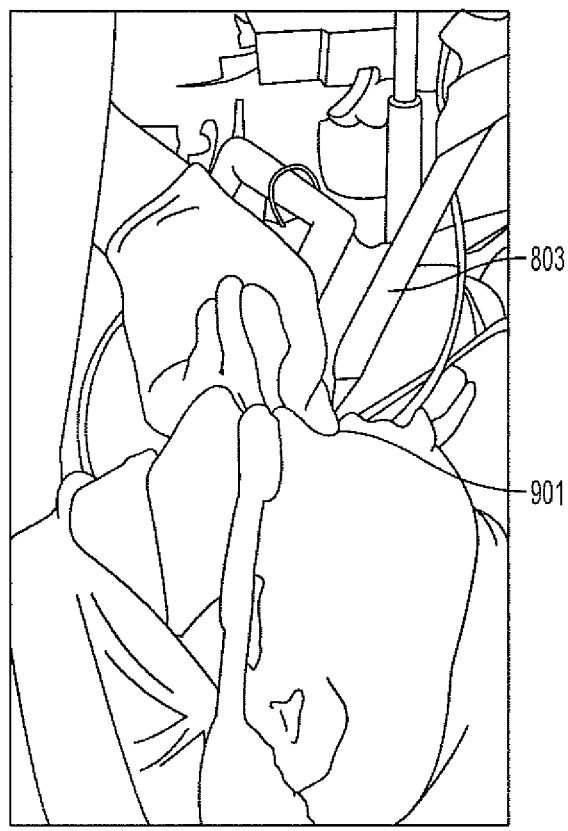
FIG. 9 provides a view of an embodiment of a PUG/TEE combination inserted into the pharynx of a patient.

The distal tip (801) of the TEE probe (803) will first be placed within the PUG (1) and will generally be inserted approximately 15 cm. The TEE probe portion performing imaging will be located inside the gel balloon (22). This placement is indicated in FIG. 8. After lubricating the external surface of the PUG, the assembly (850) of PUG (1) and TEE (803) is inserted into the patient's mouth (901) as far as the pharynx in the midline as shown in FIG. 9. The distance of introduction may be estimated by tracing an imaginary line which extends from the tip of the chin to the furcula of sternum bone or via other methods known to those of ordinary skill. The introduction can be made smoother by using known jaw lift maneuvers and easier when compared with the sole TEE (803) insertion due to the PUG device (1) being specifically shaped for placement within the pharynx. Because the PUG device (1) will generally block the pharynx when the gel balloon is filled, the procedure is generally recommended only for patients already undergoing mechanical ventilation so as not to jeopardize the respiratory process.

Upon insertion, the external compartment (72) attached to the gel balloon (22) will be squeezed, so as to move medium (131) into the balloon (22) and conform the balloon (22) to the interior of the pharynx and thus fill the pharynx with the physical medium in the balloon (22) and allow for transmission of the ultrasonic signal. The filled shaft (56) and balloon (22) also helps to keep the TEE probe (803) stable during the punction action. This can provide further benefit as the TEE probe (803) can provide continuous generally real-time monitoring of the punction.

Figure 10A:
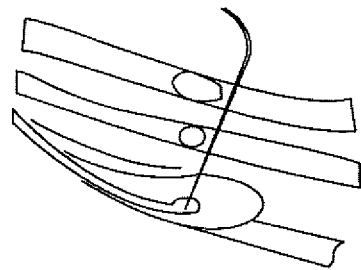
FIG. 10A provides an anatomical depiction of the pharynx, carotid artery, and jugular vein, and the position of the PUG/TEE probe in the pharynx (trans-pharyngeal ultrasound).
Figure 10B:
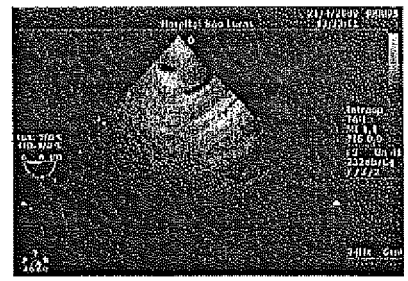
FIG. 10B provides the respective image obtained with the ultrasound emission angle between 0 and 20 degrees, disclosing the jugular vein and carotid artery in transversal view.
Figure 10C:
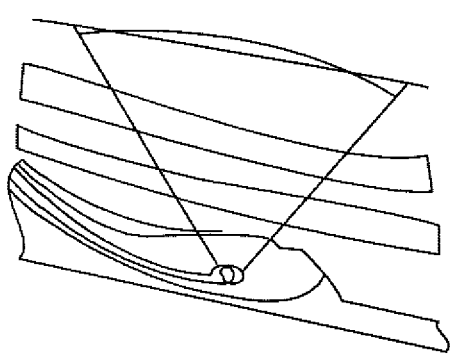
FIG. 10C provides an anatomical depiction of the pharynx, carotid artery, and jugular vein, and the position of the PUG/TEE probe in the pharynx.
Figure 10D:
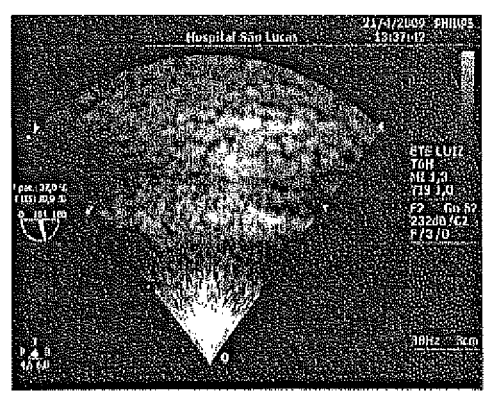
FIG. 10D provides the respective image obtained with the ultrasound emission angle between 80 and 110 degrees, disclosing the jugular vein and carotid artery in the longitudinal view.

With the multi-plane angle of the TEE between 0 and 20 degrees, the TEE can be used to visualize the jugular vein and carotid artery in a transversal view as shown in FIGS. 10A and 10B. The view is altered by rotating the TEE probe clockwise or counter clockwise in accordance with the chosen side, right or left respectively, to be imaged. After centralizing the desired structure on the screen the multi-plane angle is generally advanced to 90 degrees to obtain the longitudinal view of the target blood vessel as shown in FIGS. 10C and 10D. The procedure may become much simpler and straightforward by simply inverting right to left and upside down the screen to as to present the image in a more natural view which generates a correspondence between the ultrasound image and directions of the needle during the punction.

Figure 11A:
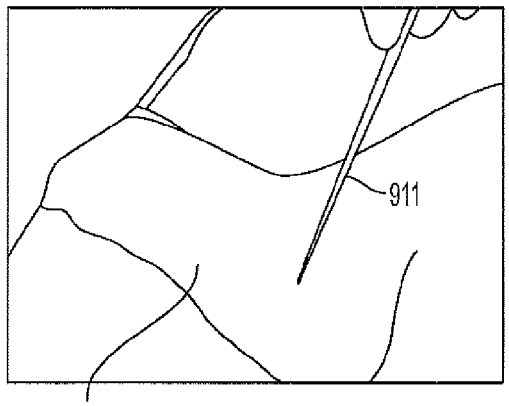
FIG. 11A provides a picture of a metallic object been slide over the patient's skin. The sliding of the metallic object over the skin generates a mechanical scan which is able to be identified by the ultrasound.
Figure 11B:
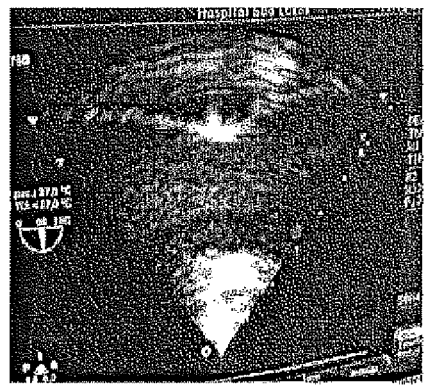
FIG. 11B provides the ultrasonic image disclosing the identification of the metallic object crossing the ultrasound beam at 90 degrees over the skin.
Figure 11C:
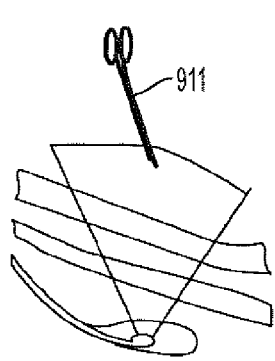
FIG. 11C provides a schematic presentation of the tip of a metallic object crossing the ultrasound beam.
Figure 11D:
FIG. 11D provides the ultrasonic image disclosing the acoustic shadow generated by the tip of the metallic object.
Figure 11E:
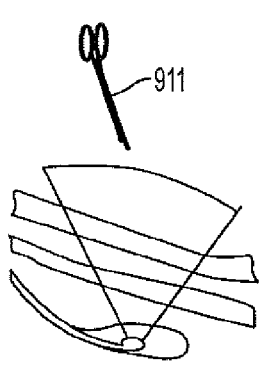
FIG. 11E provides a schematic presentation of the tip of metallic object out the ultrasound beam.
Figure 11F:
FIG. 11F provides the ultrasonic image ultrasound without the acoustic shadow.

Using a small amount of sterile gel it is then preferred that the person performing the procedure slide a flat and thin metallic object (911) (such as, but not limited to, a tweezers, needle holder, or the needle itself), over the skin (913) from the top to bottom which creates a mechanical scan able to be detected by the ultrasound. The mechanical scan generates a depression when the object crosses the ultrasound beam corresponding to an ultrasonic image. This depression is indicated in FIGS. 11B and 11D.

Owing to the high density of the particles present in the metallic objects and consequently the high acoustic impedance of them, the acoustic interface between the human tissues and the metal prevent the propagation of the ultrasound through the tissues underneath. This phenomenon generates an artifact seen in ultrasound imaging known as acoustic shadow in which an intensely echogenic line appears in the screen underneath the surface of objects with high acoustic impedance. Based on this principle, the use the metallic object crossing the ultrasound beam as discussed above provides for the ability to obtain a referential position indicator during the locating process as indicated in FIGS. 11C and 11D. It should be noted that pother solid objects could be used to provide the indicator, but solid metal objects are generally preferred as they provide for a strong image and are readily available in an operating theatre.

Figure 12A:
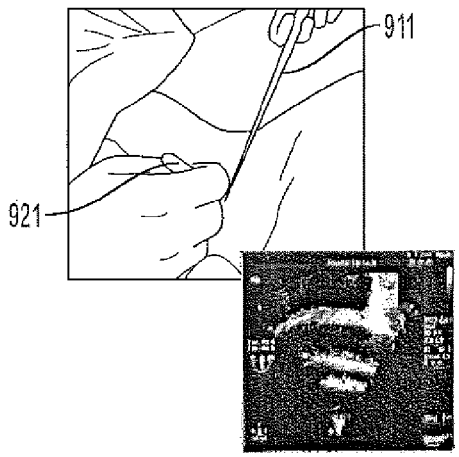
FIGS. 12A-12D provide pictures of the localizing system based on acoustic shadows created by the metallic object over the skin.
Figure 12B:
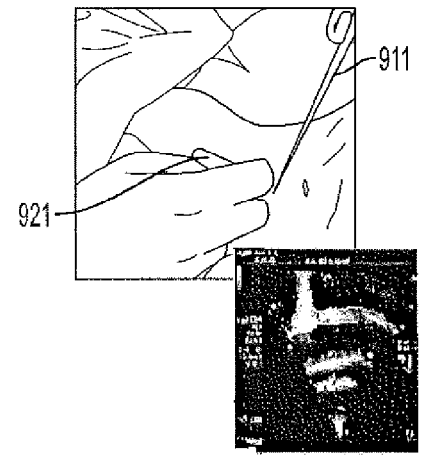
Figure 12C:
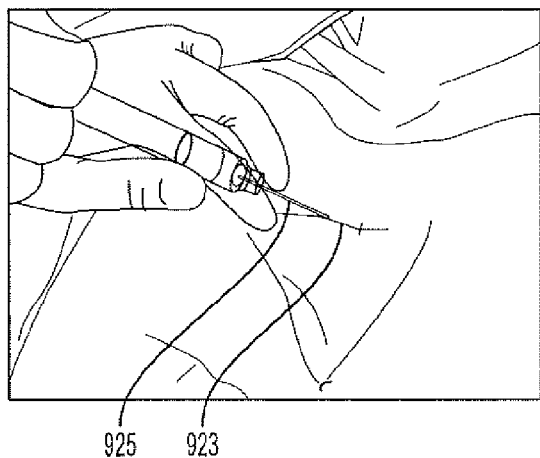
Figure 12D:
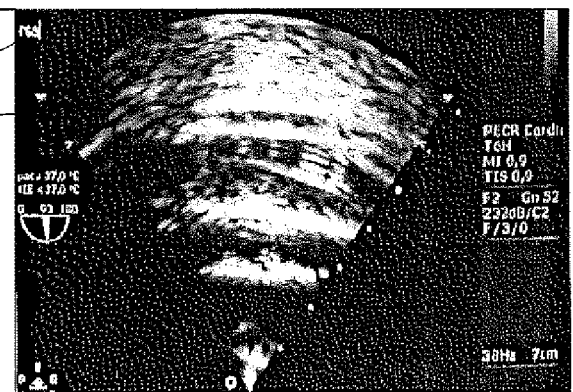
Figure 13A:
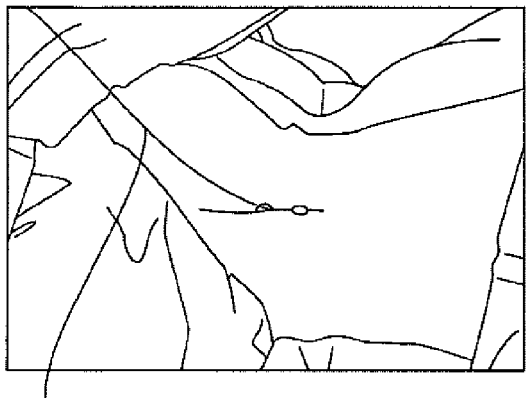
FIG. 13A provides a picture of a patient with a wire guide inserted into the jugular vein.
Figure 13B:
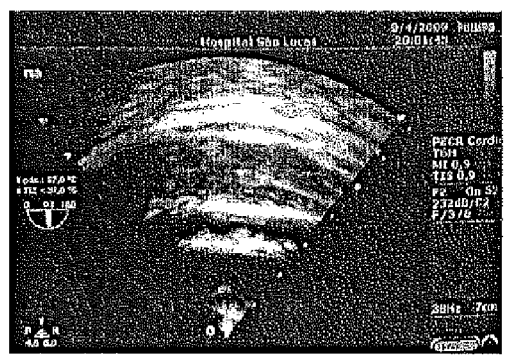
FIG. 13B provides the respective image disclosing the ultrasonic identification of the wire guide inside the jugular vein.
Figure 13C:
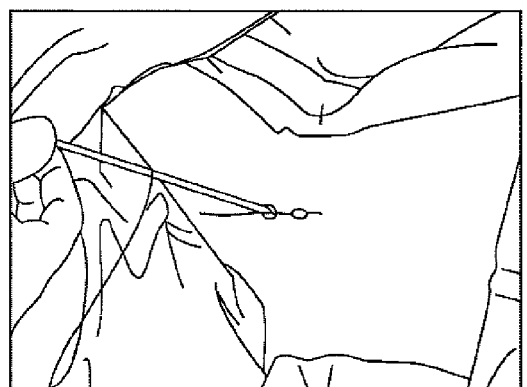
FIG. 13C provides a picture of a patient with a catheter inserted into the jugular vein.
Figure 13D:
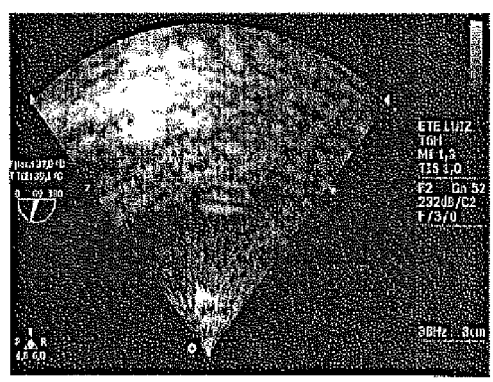
FIG. 13D provides the respective image disclosing the ultrasonic identification of the catheter inside the jugular vein.

Carrying out the above described process at two separated points in the ultrasound view (one inferior as indicated in FIG. 12A another superior as indicated in FIG. 12B) marking both points with a skin marker (921) and then tracing a connecting line (923) on the skin surface between the points as indicated in FIG. 12C, allows for the path where ultrasound beam is crossing the skin to be determined and consequently obtain the pathway in which the needle must be aligned, which is the line of FIG. 12C. Moreover, this technique enables disclosure of both the point and angle in which the needle (925) should be inserted in the skin, matching its pathway with the ultrasound beam. The deepness of insertion is titrated with the real time visualization of the needle and anatomic structures. This provides the real time view of the whole procedure. The views are provided of the needle (925) (FIGS. 12A and 12B), the wire guide (935) (FIGS. 13A and 13B), and the dilator and catheter insertion (945) (FIGS. 13C and 13D) in a generally real time fashion which may also afford the early diagnoses of catheter misplacement and avoid complications which could arise from such misplacement.

Figure 14:
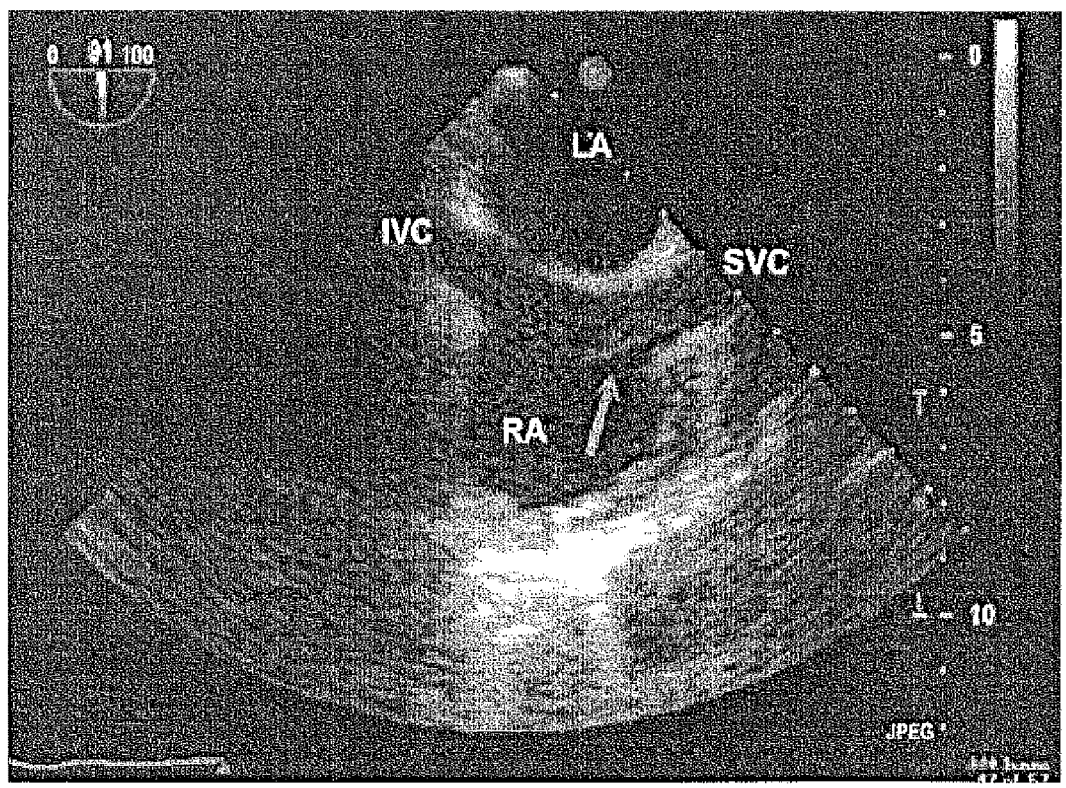
FIG. 14 provides an ultrasonographic image obtained by TEE in the bicaval view confirming the position of the tip of the catheter located in the transition of the superior vena cava (SVC) and the right atrium (RA).

Once the catheter is inserted into the jugular vein, the balloon (22) of the PUG device is generally deflated (which may occur by opening the lock (33) and by having the material (131) have a default state into the external compartment (72), or the lock (33) may simply be released and the movement of the PUG (1) may result in deflation). The PUG device (1) may then be removed by holding the probe in place and backing the PUG (1) out of the pharyngeal area. Alternatively, the PUG (1) may remain in place to provide cushioning or simply for convenience. Generally, the TEE probe (803) will be advanced into the esophagus for use in the cardiac procedure which has been setup by the placement of the catheter line. Alternatively, if the TEE probe (803) is not needed, the TEE probe (803) may be removed from the patient. Having the visualization of the bicaval view from the TEE probe (803), the position of the tip of the catheter can be adjusted and confirmed as shown in FIG. 14.

Performing the procedure above generally provides for improved visualization of the needle on its track toward the blood vessel compared to that obtained with surface ultrasounds. Further, the alignment is generally much easier to be maintained during the whole procedure as the TEE probe (803) is held in place during the procedure with the PUG (1). There is no need for a second scrubbed person to be present in the operating theater to hold the probe (803) still during the needle (925) punction.

While improved visualization is generally sufficient benefit to utilize the PUG device (1), it has also been recognized that use of the PUG device (1) provides for secondary benefits. Specifically, the TEE probe (803) is a generally rigid structure with little flexibility, therefore it frequently causes trauma in the pharynx and esophagus by its passage. Because the TEE probe (803) is rigid it may cause damage, particularly during its insertion. The pharyngeal mucosa is fragile and mechanical irritation and sore throats are common complications after the TEE exam. Major complications such as esophageal perforation, pharyngeal laceration and gastrointestinal hemorrhage are rare, but still reported in the medical literature and can occur in certain circumstances.

Owing to the mechanical proprieties of the gel balloon (22), specifically it being a relatively soft and flexible structure, even when fully inflated, it works like a cushion. This both reduces the likelihood of trauma to be caused by the TEE probe (803) being inserted into the pharynx as it provides for a protected fixed pathway spaced from the pharynx and facilitates the probe insertion through the pharynx because of the same fixed pathway of introduction. This can reduce potential complications and further add to the safety of the patients. Still further, as the fore end (15) of the PUG (1) is generally relatively enclosed by the same balloon (22) which is inserted in a partially deflated state which can result in still the gel balloon (22) also providing for cushioning of insertion of the PUG device. Further, as in the embodiment of FIGS. 5-8 the PUG (1) is generally very flexible and, therefore, much less likely to irritate neighboring structures.

While the PUG device will generally block a patient's natural airway, it is well known to those of skilled in the art, that when an individual patient is intubated and undergoing mechanical ventilation, the orotracheal tube bypasses the pharynx and delivers air into the trachea. Thus, medical devices may be inserted into the pharynx without jeopardizing the respiratory process. Following this principle, one method for using the PUG (1) will essentially completely block the pharynx, and, due to the gel-filled balloon (22), allows for ultrasonic visualization of virtually any structure of the neck.

While the above methods specifically contemplate use of the PUG (1) in visualization of needle puncture and catheter insertion, the PUG device (1) can provide for visualization of other procedures where internal imaging of the structures of the neck can be beneficial. These include, but are not limited to, guiding central line placement, per operative measurement of carotid blood flow, guiding clamp placement during carotid endarterectomy (CEA), guiding jugular bulb catheter insertion, providing real time monitoring of carotid angioplasties, cervical region biopsies, and inter-vertebral discs, and providing vertebral arteries visualization.

This device (1) may also be usable in the evaluation of atherosclerotic plaques in the carotid artery using the TEE probe (803), which already is necessary in cardiac and several non-cardiac surgeries. Having the diagnosis of the atherosclerotic artery disease in mind it might change the hemodynamic management during the general anesthesia. The PUG (1) and TEE probe (803) may also be used to measure of carotid blood flow during cardiopulmonary bypass and during carotid angioplasties. By the fact the TEE probe (803) does not make contact with the sterile field external the patient's body, it might also reduce the risk of infection and save in the operating room.

The ultrasonic views of carotid artery and jugular vein using TEE probe (803) will possibly give new emphasis to diagnostic and monitoring tools during the peri-operative period and extend the boundaries of the TEE examination thereby improving current practices. Owing to the widespread interest in TEE during the peri-operative period, many anesthesiologists are already skilled in TEE use and familiarization with PUG (1) use is expected to be relatively straightforward.

Still further, particularly in the minimally invasive robotic assisted cardiac surgery, in which the part of the extracorporeal circulation is established with the insertion of two large bore canulas introduced through the jugular vein, the PUG device (1) can also be very useful. Cerebral perfusion is one of the most important physiologic parameters to be maintained during anesthesia and especially heart surgeries in which extra-corporeal circulation (ECC) is used. For a long time, the adequacy of brain functioning has been indirectly monitored through the maintenance of global physiologic parameters, such as blood pressure, saturation and capnography.

Post operative cognitive dysfunction (POCD) has been described with high incidence after carotid and cardiac surgeries, and different neuropsychiatric syndromes have been reported: stroke (1.5 to 5.2%); postoperative delirium (10 to 30%); and short-term POCD (33 to 83%) as well as long-term POCD (20 to 60%). Brain ischemia due to emboli or low perfusion in watershed territories is considered the main guilty factor for these syndromes.

The current monitoring tools available are trans-cranial Doppler, jugular bulb and cerebral oxygen saturation. Their methodology generally relies on tardive signs of brain ischemia. Confirming the adequacy of carotid flow measurements through the TEE probe and PUG device may open new horizons for monitoring brain blood flow during the peri operative period.

Figure 15A:
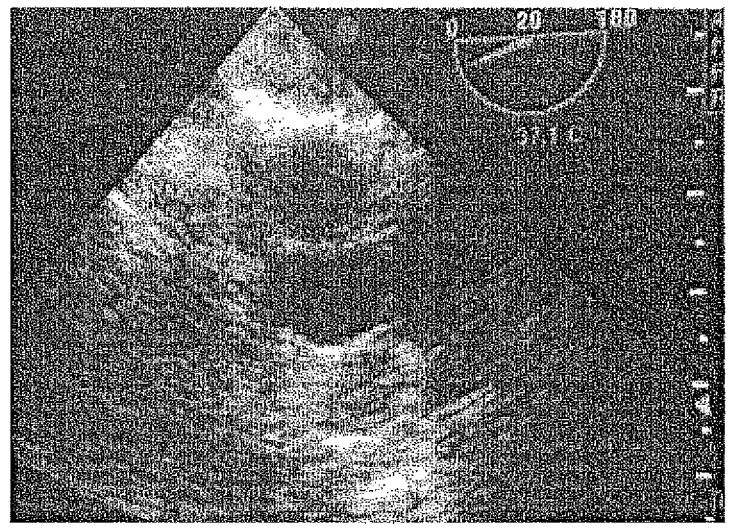
FIG. 15A provides an ultrasonic image obtained with an ultrasound emission angle between 0 and 20 degrees, disclosing the carotid artery and jugular vein in transversal view. The dotted line surrounding the inner layer of the carotid artery represents the measurement of the cross sectional area of carotid lumen done by planimmetry.
Figure 15B:
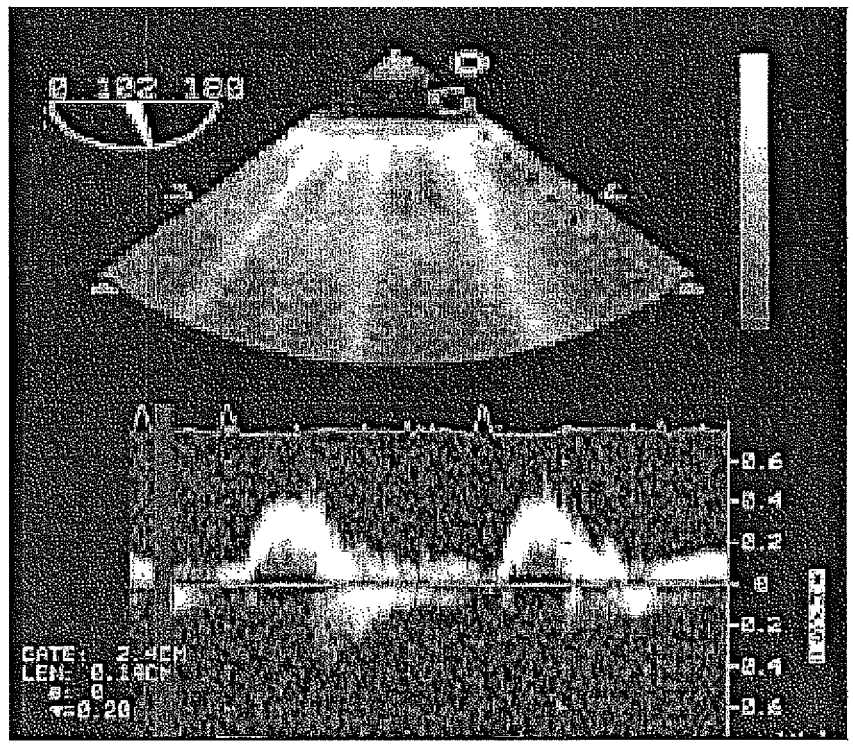
FIG. 15B provides an image obtained with an ultrasound emission angle between 80 and 110 degrees, disclosing the carotid artery in a longitudinal view and the flow velocity measurement obtained by pointing the volume sampling of the pulsed wave Doppler far lateral in the center of the carotid lumen.

Specifically, one embodiment of a methodology for carotid blood flow measurement can utilize the imaging capability of the TEE/PUG assembly (850). Upon insertion of TEE/PUG (850) into the pharynx, the fluid compartment (72) attached to the gel balloon (22) would be squeezed and locked as indicated above, so as to fill the balloon (22), and this the pharynx, with the physical medium (liquid or gel) to allow the transmission of the ultrasonic signal. The filled balloon (22) also helps to keep the TEE probe stable during carotid flow measurements. The TEE probe (803) may be turned clock-wise or counter-clockwise in accordance with the chosen side, right or left respectively. Maintaining the TEE probe (803) angle from 0 to 20 degrees discloses transversal view of the carotid artery allowing for measurement of the diameter and cross sectional area (CSA) by planimetry as shown in FIG. 15A. After centralizing the desired structure on the screen (jugular vein), the multi-plane angle is again advanced to 90 degrees to obtain the longitudinal view of the vessel as shown in FIG. 15B.

The flow velocity measurement will be obtained by pointing the volume sampling of the pulsed wave Doppler far lateral, but placed in the center of the carotid lumen in order to minimize the insonation angle effects during the measurements of the flow. Furthermore as new TEE machines often include software which is able to correct the effects of the insonation angle. The velocity time integral (VTI) and all other indices related to flow can be measured with the spectral display of the pulsed Doppler. Carotid blood flow would thus be calculated by using the formula: Carotid Flow=VTI×CSA.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A pharyngeal ultrasound guide (PUG) device, the device comprising:
   a hollow shaft comprising two ends and an elongated body therebetween, the elongated body comprising and inner layer and an outer layer with an internal space enclosed therebetween; and
   a balloon arranged at a first of said two ends, said balloon being sized and shaped for placement in a pharyngeal region of a human and having an internal volume for enclosing an ultrasound transmission medium, said internal volume being in fluid communication with said internal space between said two layers of said elongated body;
   wherein said inner layer forms a generally cylindrical hollow opening closed at said first of said two ends and said outer layer is integrally formed with an outer layer of said balloon.

2. The PUG device of claim 1, further comprising an ultrasound probe placed within said cylindrical hollow opening.

3. The PUG device of claim 2, wherein said ultrasound probe comprises a Trans-Esophageal Echocardiography (TEE) probe.

* * * * *